(12) United States Patent
Balzano

(10) Patent No.: US 7,878,055 B2
(45) Date of Patent: Feb. 1, 2011

(54) SENSOR AND ANALYZER FOR DETERMINING PHYSIOLOGICAL LIMITATIONS

(76) Inventor: Alfiero Balzano, 11371 Monarch St., Garden Grove, CA (US) 92841

(*) Notice: Subject to any disclaimer, the term of this patent is extended or adjusted under 35 U.S.C. 154(b) by 16 days.

(21) Appl. No.: 11/438,494

(22) Filed: May 22, 2006

(65) Prior Publication Data

US 2006/0282018 A1    Dec. 14, 2006

Related U.S. Application Data

(60) Provisional application No. 60/683,077, filed on May 23, 2005.

(51) Int. Cl.
*A61B 5/00* (2006.01)
*A61B 5/103* (2006.01)
*G08B 23/00* (2006.01)

(52) U.S. Cl. .................. 73/172; 73/865.4; 600/592; 340/573.1; 340/573.7

(58) Field of Classification Search ............ 482/1, 482/8, 9, 900, 902; 600/587, 595; 602/16; 73/865.4, 172; 340/573.1, 573.7
See application file for complete search history.

(56) References Cited

U.S. PATENT DOCUMENTS

| | | | | |
|---|---|---|---|---|
| 4,858,620 A | * | 8/1989 | Sugarman et al. ........... 600/587 |
| 5,078,152 A | * | 1/1992 | Bond et al. ................. 600/587 |
| 5,243,998 A | * | 9/1993 | Silverman et al. ........... 600/595 |
| 5,642,096 A | * | 6/1997 | Leyerer et al. ........... 340/573.1 |
| 6,273,863 B1 | * | 8/2001 | Avni et al. .................. 600/587 |
| 6,739,878 B1 | * | 5/2004 | Balzano ....................... 439/67 |
| 6,872,187 B1 | * | 3/2005 | Stark et al. .................... 602/16 |
| 6,913,558 B2 | * | 7/2005 | Mori et al. ..................... 477/3 |
| 7,072,789 B2 | * | 7/2006 | Vock et al. .................. 702/141 |
| 2003/0013580 A1 | * | 1/2003 | Limonadi ..................... 482/45 |
| 2004/0019382 A1 | * | 1/2004 | Amirouche et al. ...... 623/18.11 |

* cited by examiner

*Primary Examiner*—Loan Thanh
*Assistant Examiner*—Sundhara M Ganesan
(74) *Attorney, Agent, or Firm*—Stetina Brunda Garred & Brucker

(57) ABSTRACT

A sensing and analyzing device for determining when physical limits of a patient have been exceeded by the patient during exercise is provided. The device may comprise a sensing unit, analyzing unit and a warning unit. The sensing unit may be attached to critical locations on a body of the patient. The sensing unit may be operative to sense pressure. The analyzing unit may be attached to a convenient location on the patient's body. The analyzing unit may be operative to receive pressure data from the sensing unit to determine whether the patient has exceeded the physical limits of the patient. The warning unit may communicate with the analyzing unit and be activated by the analyzing unit when the physical limit of the patient has been exceeded for notifying the patient when the patient's physical limits have been exceeded.

57 Claims, 2 Drawing Sheets

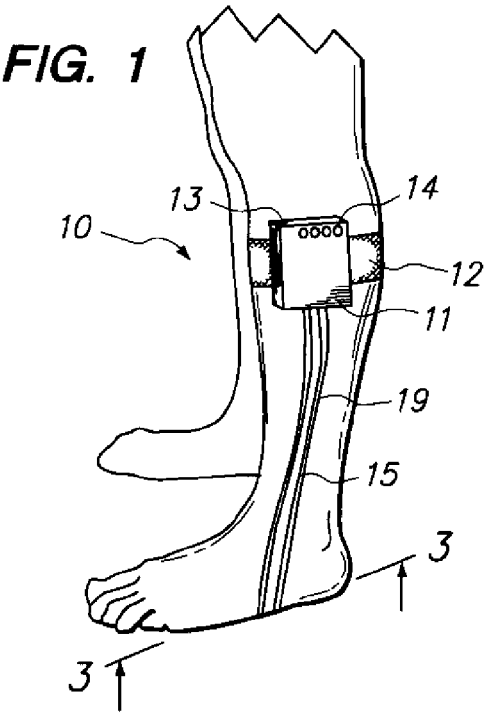
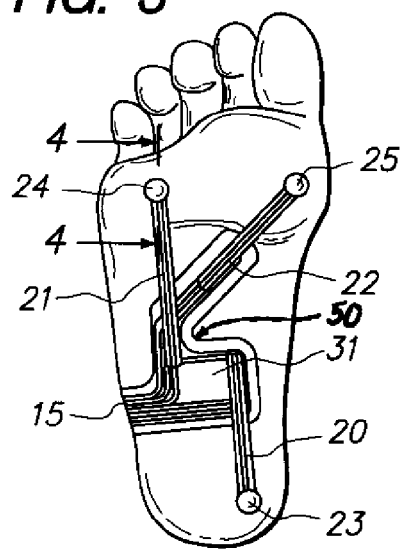
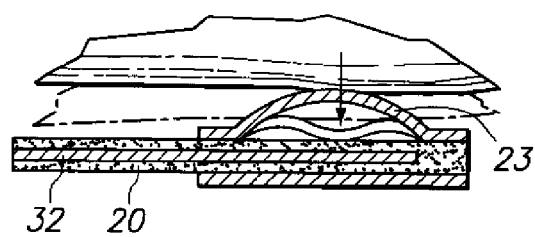
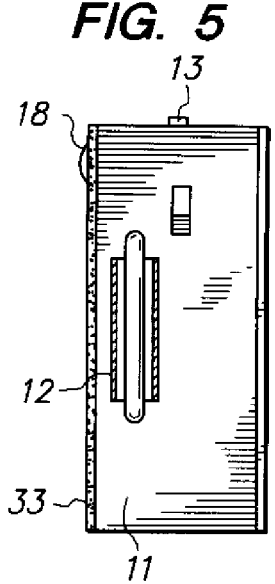
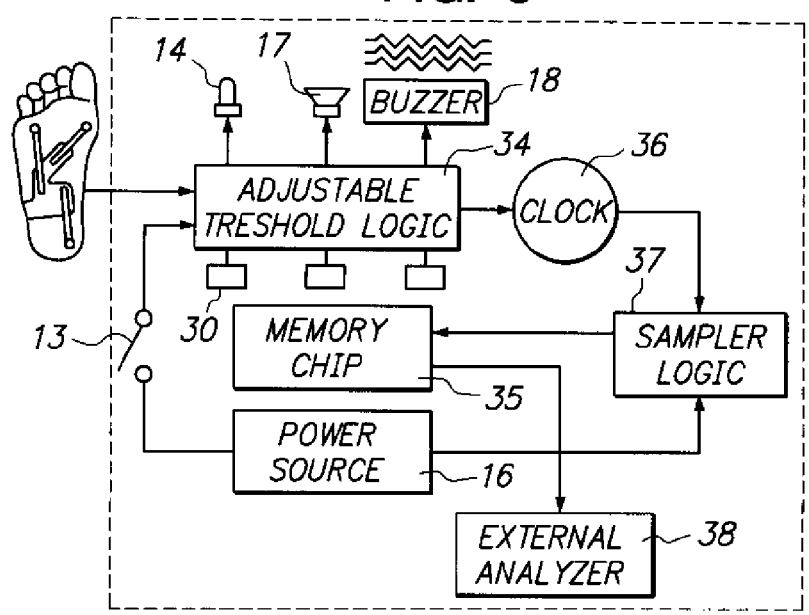

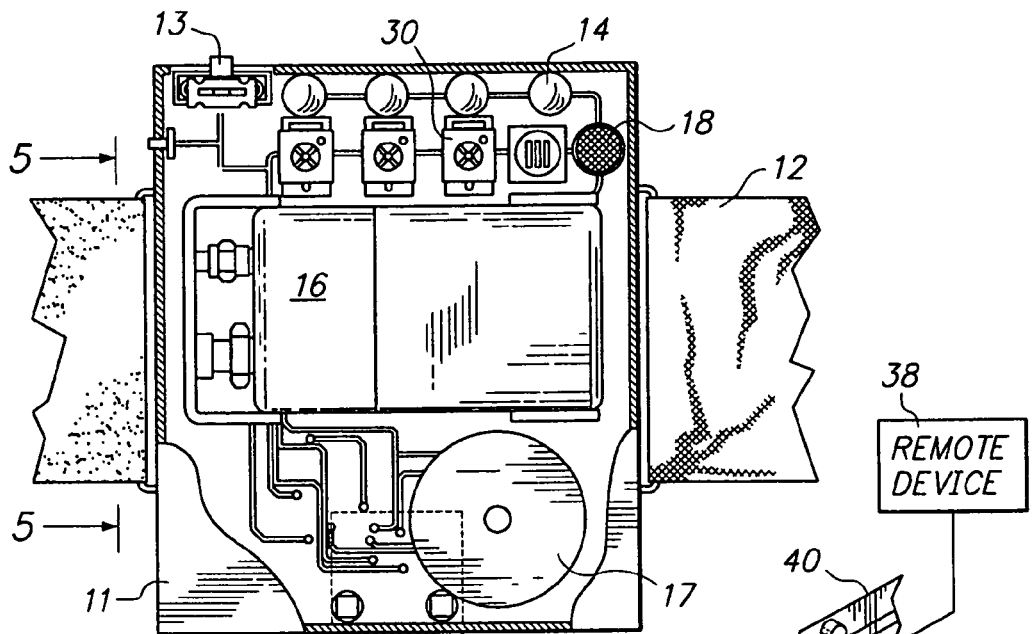
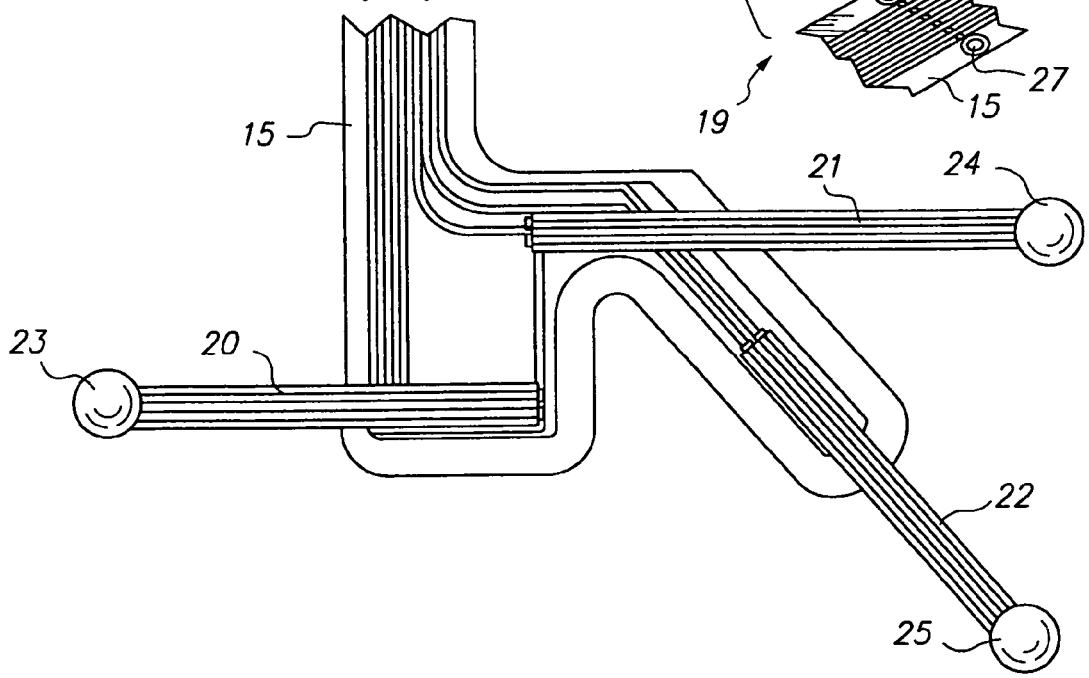

SENSOR AND ANALYZER FOR DETERMINING PHYSIOLOGICAL LIMITATIONS

CROSS-REFERENCE TO RELATED APPLICATIONS

This application claims the benefits of U.S. provisional patent application Ser. No. 60/683,077, filed May 23, 2005, the entire contents of which is expressly incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates to the field of sensing and analyzing devices and more particularly to a novel device which is worn by a patient for dynamic sensing and recording of physiological information while under stress in order to prevent the patient from exceeding predetermined physical limitations.

2. Description of the Prior Art

In the past, it has been the conventional practice for persons engaging in recovery physical therapy to exercise by running, walking, or employing other physical procedures in which the person is under stress and may exceed physical limits which will adversely affect recovery and may even cause damage. For example, a person having a leg or arm injury may be advised to perform daily exercise of the limb in order to aid recovery. In following such a procedure, the limb is placed under stress, and the muscles, ligaments and other tissues may not have recovered in sufficiency to permit overload or excessive exercise. Such excessive experience may cause additional stress and may even physically damage the muscles or other body organs which are intended to be conditioned.

Therefore, a long-standing need has existed to provide a sensing and analyzing apparatus that would sense, analyze and monitor the person's physical condition while under stress. A warning device is included in the apparatus whereby the person may be notified when the physical limits for his particular condition has been reached or exceeded.

SUMMARY OF THE INVENTION

Accordingly, the above problems and difficulties are avoided by the present invention which employs a sensor and analyzing device which is releasably worn on the limb of the user and that includes a plurality of pressure pad sensors strategically located, such as on the sole of the user's foot. The plurality of sensors are connected to an analyzer unit by means of a flexible cable wherein the cable may be adjustable in length for comfort and wearability. The analyzer unit includes an adjustable threshold logic circuit for setting limits not to be exceeded by the user during an exercising procedure. A memory network is included for storing information derived during the exercise procedure and a sampler logic circuit which is connected to a clock is coupled between the adjustable threshold logic and the memory network so that periodic information is sampled and placed into the memory network according to a preset timing schedule. Alarm means include visual, audible and vibratory devices coupled to the adjustable threshold logic so that the user may be alerted when exercising limits have been approached or exceeded. Furthermore, an external analyzer remotely located, such as in a physician's office, may be attached to the memory network via the flex cable for receiving the results of information stored during the full memory network so that periodic information is sampled and placed into the memory network according to a preset timing schedule. Alarm means include visual, audible and vibratory devices coupled to the adjustable threshold logic so that the user may be alerted when exercising limits have been approached or exceeded. Furthermore, an external analyzer remotely located, such as in a physician's office, may be attached to the memory network via the flex cable for receiving the results of information stored during the full exercise procedure.

In an aspect of the sensor and analyzing device, a physiological sensing and analyzing device that is strategically located on the body of a patient undergoing physical exercise for alerting the user to cease exercising as his or her physical limit is close or beyond preset limits is provided.

In another aspect of the physiological sensing and analyzing device, a novel medical device for alerting a patient during an exercise procedure that his physiology is in jeopardy due to his exceeding physical limits as determined by a physician's standards is provided.

In still another aspect of the physiological sensing and analyzing device, a novel sensing and analyzing medical device adapted to be worn by a person undergoing physical stress which will notify the wearer that further exercise or further intensity of exercise is approaching the limits of stress necessary for recovery is provided.

In yet another aspect of the physiological sensing and analyzing device, an alarm system on a sensor and analyzing device adapted to be comfortably worn by a patient so that the patient will be notified and alerted by sound, vibrations, or visually, that he is approaching or has exceeded physical limitations is provided.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a perspective view illustrating the novel sensor and analyzing device in use on a limb of a patient;

FIG. 2 is an enlarged side elevational view, partly in section, of the sensor and analyzing device shown in FIG. 1;

FIG. 3 is a bottom view of a patient's sole illustrating placement of sensors in critical locations;

FIG. 4 is an enlarged sectional view of a typical sensor as employed in the sensor arrangement shown in FIG. 3 as taken in the direction of arrows 4-4 thereof;

FIG. 5 is a side elevational view of the analyzer unit shown in FIG. 1 and illustrating a retaining strap, in sectional view;

FIG. 6 is a block diagram illustrating the arrangement of circuit and network relationships for the sensor and the analyzer unit; and FIG. 7 is an enlarged perspective view illustrating the adjustable connection to lengthen or shorten the flex cable extended between the sensors as shown in FIG. 3 and the analyzing unit as shown in FIG. 2, as well as providing connection for external analyzer equipment.

DESCRIPTION OF PREFERRED EMBODIMENT

Referring now to FIG. 1, the novel sensor and analyzing device is illustrated in the general direction of arrow 10 which includes a case or housing 11 which is carried on a portion of the patient or user's body, such as the user's leg. For illustrative purposes, the device 11 is carried adjacent to the user's lower leg and is held thereon by a strap 12 which temporary secures the case or housing 11 in a suitable position and location. An on/off switch 13 is available for depression by the user in order to control the operation of the device. The device includes an alarm means which, in one form, may take the embodiment of a visual signal, such as energizing of lights, such as light 14. An elongated flex cable is indicated by numeral 15 which may include a lower portion and an upper portion releasably coupled together by connectors 19. The flex cable includes a plurality of conductor runs leading from a sensor means, as shown in FIG. 3, to a circuit board in the housing 11.

Referring now in detail to FIG. 2, the housing 11 encloses various components of the unit which includes a nine-volt battery 16, the switch 13, and a plurality of LED lights which includes light 14. In addition to the LED's in the alarm means, an audible alarm 17 is included as well as a buzzer 18 which provides a vibratory signal. The buzzer resides adjacent the user's body so that the vibrating signal will alert the user in the same manner that the lights 14 and/or the audible signal 17 does.

It can also be seen in FIG. 2 that the elongated flex cable 15 is attached to the connectors of a circuit board within the unit or housing 11 and that the flex cable terminates in a sensing means at its opposite distal end. The sensing means includes a base pad 50 and short lengths of flex cable, such as indicated by numerals 20, 21, and 22 which terminate in sensing pads 23, 24, and 25. The elongated flex cable 15 may be provided with connectors along its length so as to permit length adjustment of the flex cable in order to accommodate the placement of the housing 11 in a critical location on the user's body. Connector points 26 and 27 may be placed at suitable locations along the length of the elongated flex cable 15 to permit shortening or lengthening of the cable, as well as being useful in connecting with external or remote devices. Also these connections or points may take the form of those disclosed in the U.S. Letters Patents 6,739,878. Sensitivity adjustments means, such as indicated by numeral 30, are provided.

Referring now in detail to FIG. 3, it can be seen that the sensing means is carried on the distal end of cable 15 and is represented by the numeral 31. As illustrated, it can be seen that the pressure pads 23, 24 and 25 are placed at strategic or critical locations on the bottom or sole of the user's foot. For example, sensor pad 23 is placed on the heel of the user's foot, while pads 24 and 25 are placed immediately behind the toes of the foot.

Referring now in detail to FIG. 4, an enlargement is shown of pressure pad 23 which is illustrated in broken lines in a depressed condition when the weight of the user is applied to the sensor. The pressure is transferred through the cladding of the cable segment 20 to change the resistance in a conductor 32 which is then introduced to the analyzing portion of the system. Similar resistance changes or modifications are created by the depression of pads 24 and 25 which are combined in the analyzing portion of the system.

In FIG. 5, it can be seen that the buzzer 18 is exposed on the back of the housing 11 so as to touch the skin of the user. Thereby, any vibration of the buzzer will notify the user that threshold levels of exercise are being exceeded or approached. Also, a cushion pad 33 is placed on the backside of housing 11 so as to provide comfort when the housing is worn on the limb or other portion of the user's body.

Referring now in detail to FIG. 6, it can be seen that the change of resistance signals from the sensors 23-25 inclusive are introduced to an adjustable threshold logic network 34 which are then transferred to a memory chip 35 for storage and comparison with previously stored statistical data. The transfer is through a clock 36 and a sampler logic network 37 so that introduction of the signals is made in a timed sequence. A power source 16 is represented by the battery. For remote review of the statistical material stored on the memory chip 35, an external analyzer 38 is used. The external analyzer may be detachably connected to the system using the connectors 26 and 27 and such a connection 19 is further illustrated in FIG. 7.

In FIG. 7, the remote device, such as the analyzer 38, may be detachably connected by means of a flexible cable 40 having prongs 41 and 42 which are inserted into the connector receptacles 26 and 27 respectively.

In view of the foregoing, it is to be noted that the flex interconnection allows for easy replacement and also that the control pads allow expansion for load-bearing sensitivity. The flex cable has an adjustment connector and that each sensor can be positioned to match the size of the user's foot.

The device may be placed on a patient having a foot, leg, knee, and/or hip injury, for example, or on a limb requiring corrective surgery. The device may be strapped in a critical location so as to sound or alarm when the patient has exceeded a doctor prescribed maximum range of motion, which may be caused by a shift in weight and/or angle of stance. In this manner, the device may determine the physiological orientation of the patient. The use of pressure sensitive pads whose resistance or voltage output changes depending upon the amount of pressure placed on the sensor area is incorporated into the instrumentation. After defining the electrical outputs of a desired sensor material, as relating to the calculated weight span of a normal human being, an electrical circuit allowing for variable sensor positioning is employed where the electric outputs can be continuously monitored by computer logic circuits.

The circuitry allows for an adjustable threshold to be set and may be determined by a physician, the setting of which, when reached, activates an alarm, such as a vibrating unit like a buzzer, placed against the skin of the user or may employ a visual LED light and/or a siren alarm. The electronics operate on a standard replaceable 9-volt DC battery 16.

The electronics are inclusive of an electronic clock set by the physician to activate a "sampler" circuit, where the sensor information is automatically sampled remotely at the physician's remote computer. The sampling is programmed in time and stored in a memory chip so that when the patient returns to the doctor's office, the doctor can download the sample data and review the same for diagnosis purposes. The electronic sampler can further be programmed using specially developed software to identify special instructions from/to the physician, such as temperature, pressure, etc. Additional proven ceramic sensors can be added to the same insole and positioned to take an ultrasonic view of the stressed area when the sample is taken as defined by the physician and stored in the memory, and again, download and the picture printed for later review by the physician.

The electronic package unit 11 has been designed so as to be small in size and to fit the patient's extremity or limb or other body portion and uses soft adjustment bands to retain the device in position. The interconnect or flex cable has an "adjustable length feature" making use of pressure point contact or flexible cable connectors, as disclosed in U.S. Pat. No.

6,739,878. The electronic sensor data is communicated from the variable location of the sensors on the bottom of the limb up to the conductors of a flat, flexible polyimide insulated cable to a connector-less pressure point set of connections entering the bottom of the computer logic board in the housing 11. As can be seen, the computer logic board may be reused while the sensor flexible cable circuit is easily detached from the connector-less interconnect and readily replaced.

The sensors and flat flexible conductor may be mounted in a more rigid limb conforming support, such as an insole which conforms to the patient's foot and/or can be mounted in a cast as determined by the physician.

The product incorporating the present invention has many areas of application but most urgent applications involve foot surgery and recovery therefrom.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A sensing and analyzing device for determining when a patient has exceeded a range of motion during exercise, the device comprising:
   a. a sensing unit including a base pad having a plurality of first flex cables extending therefrom, and a plurality of spaced pressure pads connectable to the bottom of a patient's foot, each pressure pad being engaged to a respective first flex cable and configured to separately sense pressure applied by the patient proximate each pressure pad, the plurality of spaced pressure pads configured to each generate a responsive electrical pressure signal, the pressure signals being collectively representative of the a relative distribution of pressure on a patient's foot;
   b. an analyzing unit attachable to a convenient location on the patient's body, the analyzing unit includes adjustable threshold logic operative to receive the pressure signals from the sensing unit to determine whether the relative distribution of pressure on a patient's foot relates to a physiological orientation that exceeds the range of motion; and
   c. a warning unit being communicable with the analyzing unit and being activatable by the analyzing unit when the range of motion has been exceeded for notifying the patient when the range of motion has been exceeded.

2. The device of claim 1 wherein the plurality of pressure pads have a domed configuration which applies pressure to a conductor in the respective first flex cable when a force is applied to the pressure pads to change a resistance of the conductor.

3. The device of claim 1 further comprising a second flex cable for providing a communication pathway between the sensing unit and the analyzing unit to transfer data from the sensing unit to the analyzing unit.

4. The device of claim 3 wherein the second flex cable comprises:
   a. an upper portion communicable with the analyzing unit;
   b. a lower portion communicable with the sensing unit and the upper portion; and
   c. connector attached to the upper portion and the lower portion for detachably connecting the upper portion to the lower portion.

5. The device of claim 4 further comprising a remote device connectable to the connectors of the upper portion for downloading data stored in a memory of the analyzing unit.

6. The device of claim 3 wherein the second flex cable is conformable to the leg of a user.

7. The device of claim 3 wherein the second flex cable lower portion and the base pad are formed as an integral flex cable.

8. The device of claim 1 further comprising a remote device connectable to the analyzing unit for downloading data stored in a memory of the analyzing unit.

9. The device of claim 1 wherein the analyzing unit comprises:
   i. a memory for storing sensed data received from the sensing unit; and
   ii. a clock and a sampler logic network for transferring data from the sensing unit to the memory in a timed sequence.

10. The device of claim 1 wherein the warning unit comprises a buzzer, audio alarm, a light, or combinations thereof.

11. The device of claim 1 further comprising a strap connected to the analyzing unit for attaching the analyzing unit to the patient.

12. The device of claim 1 wherein the sensing unit is configured to generate pressure data in response to sensing pressure.

13. The device of claim 12 further comprising a memory unit in electrical communication with the sensing unit for storing the pressure data.

14. The device of claim 13 wherein the memory unit is further operative to compare the pressure data with previously stored pressure data.

15. The device of claim 1 wherein the sensing unit measures the weight of the patient.

16. The device of claim 1 wherein the sensing unit measures the angle of the patient's stance.

17. The device of claim 1 wherein the sensing unit measures the distribution of the patient's weight on the foot of the patient.

18. The device of claim 1 wherein each pressure pad is configured to sense pressure proximate a specific area of the patient's foot.

19. The device of claim 18 wherein each pressure pad is configured to sense pressure in different areas of the patient's foot.

20. The device of claim 19 wherein the different areas of the patient's foot includes a heel portion and a portion located immediately behind a plurality of toes, the sensing unit including three pressure pads, two of the three pressure pads configured to sense pressure on the portion immediately behind the toes and one of the three pressure pads configured to sense pressure on the heel portion.

21. The device of claim 1 wherein the analyzing unit is disposable below a user's knee adjacent a lower leg of the user.

22. The device of claim 1 wherein a change in relative electrical pressure signals from the pressure pads is representative of a shift in weight on the patient's foot.

23. The device of claim 1 wherein a change in relative electrical pressure signals from the pressure pads is representative of a shift in angle of stance of the patient.

24. The device of claim 1 wherein the base pad is configured to extend along the bottom of the patient's foot.

25. The device of claim 1 wherein the sensing unit is configured to extend along the bottom of the patient's foot.

26. A sensing and analyzing device for determining a physiological condition of a patient, the device comprising:
- a sensing unit including a base pad having a plurality of first flex cables extending therefrom, and a plurality of pressure pads attachable to spaced locations on the bottom of the patient's foot, each pressure pad being engaged to a respective first flex cable and operative to separately generate a responsive electrical output in response to pressure applied by the patient while standing or walking; and
- an analyzing unit in communication with the sensing unit, the analyzing unit being operative to receive electrical outputs generated by the plurality of pressure pads and to derive a relative distribution of pressure on the patient's foot;
- the analyzing unit including adjustable threshold logic for determining whether a physiological limit has been exceeded.

27. The device of claim 26 wherein the relative distribution of pressure on the patient's foot is derived from analysis of relative pressure applied to the pressure pads.

28. The device of claim 26 wherein the relative distribution of pressure on the patient's foot includes angle of stance information.

29. The device of claim 26 wherein the relative distribution of pressure on the patient's foot includes information concerning a shift in the patient's angle of stance.

30. The device of claim 26 wherein the relative distribution of pressure on the patient's foot includes patient range of motion information.

31. The device of claim 26 further including a warning unit in electrical communication with the analyzing unit and activatable by the analyzing unit in response to pressure pads outputs indicating that the patient has exceeded a predetermined physical limit.

32. The device of claim 26 further comprising a second flex cable for providing a communication pathway between the sensing unit and the analyzing unit to transfer data from the sensing unit to the analyzing unit.

33. The device of claim 32 wherein the second flex cable comprises:
- an upper portion communicable with the analyzing unit;
- a lower portion communicable with the sensing unit and the upper portion; and
- connector attached to the upper portion and the lower portion for detachably connecting the upper portion to the lower portion.

34. The device of claim 32 wherein the second flex cable is conformable to the leg of a user.

35. The device of claim 26 wherein the analyzer unit samples pressure pad outputs in accordance with a preset timing schedule.

36. The device of claim 26 wherein the physiological information is derived from a comparison of pressure pad outputs to stored information representative of patient physical limits.

37. The device of claim 26 wherein the analyzer is adapted to be worn by the patient.

38. The device of claim 26 wherein the analyzer is located remote from the patient.

39. The device of claim 26 wherein each pressure pad is configured to sense pressure proximate a specific area of the patient's foot.

40. The device of claim 39 wherein each pressure pad is configured to sense pressure in a different area of the patient's foot.

41. The device of claim 40 wherein two of the pressure pads are configured to sense pressure on the portion immediately behind the patient's toes and one of the pressure pads is configured to sense pressure on the patient's heel portion.

42. The device of claim 26 wherein the analyzing unit is disposable below a user's knee adjacent a lower leg of the user.

43. A sensing and analyzing device for determining a shift in an angle of stance of a patient, the device comprising:
- a sensing unit including a base pad having a plurality of first flex cables extending therefrom, and a plurality of pressure pads attachable to spaced locations on the bottom of the patient's foot, each pressure pad being engaged to a respective first flex cable and operative to separately generate a responsive electrical output in response to pressure applied by the patient while standing or walking; and
- an analyzing unit in communication with the sensing unit, the analyzing unit being operative to receive electrical outputs generated by the plurality of pressure pads and to derive a relative distribution of pressure on the patient's foot;
- the analyzing unit including adjustable threshold logic for determining whether a maximum shift in the patient's angle of stance has been exceeded.

44. The device of claim 43 wherein the relative distribution of pressure on the patient's foot is derived from analysis of relative pressure applied to the pressure pads.

45. The device of claim 43 wherein the relative distribution of pressure on the patient's foot includes information concerning a shift in the patient's angle of stance.

46. The device of claim 43 wherein the relative distribution of pressure on the patient's foot includes patient range of motion information.

47. The device of claim 43 further including a warning unit in electrical communication with the analyzing unit and activatable by the analyzing unit in response to pressure pads outputs indicating that the patient has exceeded a physical limit.

48. The device of claim 43 further comprising a second flex cable for providing a communication pathway between the sensing unit and the analyzing unit to transfer data from the sensing unit to the analyzing unit.

49. The device of claim 48 wherein the second flex cable comprises:
- an upper portion communicable with the analyzing unit;
- a lower portion communicable with the sensing unit and the upper portion; and
- connector attached to the upper portion and the lower portion for detachably connecting the upper portion to the lower portion.

50. The device of claim 43 wherein the analyzer unit samples pressure pad outputs in accordance with a preset timing schedule.

51. The device of claim 43 wherein the physiological information is derived from a comparison of pressure pad outputs to stored information representative of patient physical limits.

52. The device of claim 43 wherein the analyzer is adapted to be worn by the patient.

53. The device of claim 43 wherein the analyzer is located remote from the patient.

54. The device of claim 43 wherein each pressure pad is configured to sense pressure proximate a specific area of the patient's foot.

55. The device of claim 54 wherein each pressure pad is configured to sense pressure in different areas of the patient's foot.

56. The device of claim 55 wherein two of the pressure pads are configured to sense pressure on the portion immediately behind the patient's toes and one of the-pressure pads is configured to sense pressure on the patient's heel portion.

57. The device of claim 43 wherein a change in relative electrical pressure signals from the pressure pads is representative of a shift in weight on the patient's foot.

* * * * *